United States Patent
Oh et al.

(10) Patent No.: US 8,789,425 B2
(45) Date of Patent: Jul. 29, 2014

(54) MICRO/NANO-MECHANICAL TEST SYSTEM EMPLOYING TENSILE TEST HOLDER WITH PUSH-TO-PULL TRANSFORMER

(71) Applicant: Hysitron Inc., Eden Prairie, MN (US)

(72) Inventors: Yunje Oh, Medina, MN (US); Edward Cyrankowski, Woodbury, MN (US); Zhiwei Shan, Plymouth, MN (US); Syed Amanula Syed Asif, Bloomington, MN (US)

(73) Assignee: Hysitron Incorporated, Eden Prairie, MN (US)

( * ) Notice: Subject to any disclaimer, the term of this patent is extended or adjusted under 35 U.S.C. 154(b) by 0 days.

(21) Appl. No.: 13/888,959

(22) Filed: May 7, 2013

(65) Prior Publication Data
US 2013/0247682 A1    Sep. 26, 2013

Related U.S. Application Data

(63) Continuation of application No. 12/575,368, filed on Oct. 7, 2009, now Pat. No. 8,434,370.

(60) Provisional application No. 61/103,456, filed on Oct. 7, 2008.

(51) Int. Cl.
*G01L 1/00* (2006.01)

(52) U.S. Cl.
USPC .......................................................... 73/774

(58) Field of Classification Search
USPC .......................................................... 73/774
See application file for complete search history.

(56) References Cited

U.S. PATENT DOCUMENTS

| | | |
|---|---|---|
| 5,060,519 A | 10/1991 | Chojitani et al. |
| 6,466,678 B1 | 10/2002 | Killion et al. |
| 6,817,255 B2 | 11/2004 | Haque et al. |
| 6,891,657 B2 | 5/2005 | Hewlett et al. |

(Continued)

FOREIGN PATENT DOCUMENTS

WO        00/28277        5/2000

OTHER PUBLICATIONS

Non-Final Office Action mailed Feb. 10, 2012 in U.S. Appl. No. 12/575,368.

(Continued)

*Primary Examiner* — Lisa Caputo
*Assistant Examiner* — Octavia D. Hollington
(74) *Attorney, Agent, or Firm* — Dicke, Billig & Czaja, PLLC

(57) ABSTRACT

A micromachined or microelectromechanical system (MEMS) based push-to-pull mechanical transformer for tensile testing of micro-to-nanometer scale material samples including a first structure and a second structure. The second structure is coupled to the first structure by at least one flexible element that enables the second structure to be moveable relative to the first structure, wherein the second structure is disposed relative to the first structure so as to form a pulling gap between the first and second structures such that when an external pushing force is applied to and pushes the second structure in a tensile extension direction a width of the pulling gap increases so as to apply a tensile force to a test sample mounted across the pulling gap between a first sample mounting area on the first structure and a second sample mounting area on the second structure.

20 Claims, 14 Drawing Sheets

(56) References Cited

U.S. PATENT DOCUMENTS

| | | | |
|---|---|---|---|
| 6,985,278 | B2 | 1/2006 | Chu et al. |
| 7,165,445 | B2 | 1/2007 | Bocek et al. |
| 7,425,698 | B2 | 9/2008 | Warren et al. |
| 7,441,465 | B2 | 10/2008 | Oliver et al. |
| 7,681,459 | B1 | 3/2010 | Yang et al. |
| 7,752,916 | B2 | 7/2010 | Han et al. |
| 7,878,071 | B2 | 2/2011 | Greer |
| 2003/0057993 | A1 | 3/2003 | Haque et al. |
| 2007/0157711 | A1 | 7/2007 | Bocek et al. |
| 2011/0025350 | A1* | 2/2011 | Clark .......................... 324/679 |

OTHER PUBLICATIONS

Anczykowski, et al., Analysis of the Interaction Mechanisms in Dynamic Mode SFM by means of Experimental Data and Computer Simulation, Applied Physics A, vol. 66, 1998 5 pages.

Oliver, et al., An Improved Technique for Determining Hardness and Elastic Modulus Using Load and Displacement Sensing Indentation, J. Mater, vol. 7, No. 6, Jun. 1992, pp. 1564-1583.

Gerberich, et al., Fundamental Aspects of Friction and Wear Contacts in (100) Surfaces, Fall MRS Meeting Symposium Q, vol. 649, Nov. 27-30, 2001, 12 pgs.

Asylum Research, MFP-3D Stand Alone, Asylum Research, 2008, 6 pgs.

Xiao, et al., Nanotensile Characteristics of Metal Wires, Hysitron Incorporated, 2007, 2 pgs.

Hysitron, PI 95 TEM PicoIndenter, 2008, 2 pgs.

Nano Analytics NMBH, Q-Control, 2008, 4 pgs.

Vanlandingham, et al., Review of Instrumented Indentation, Journal of Research of the National Institute of Standards and Technology, vol. 108, No. 4, Jul.-Aug. 2003, pp. 249-265.

Fischer-Cripps, Nanoindentation, Springer Book 2004 Edition, 263 pgs.

Zhu, et al., Experimental Techniques for the Mechanical Characterization of One-Dimensional Nanostructures, Experimental Mechanics, 2007, #47, 7-24.

Liu, et al., A Micro-tensile Method for Measuring Mechanical Properties of MEMS materials, Journal of Micromechanics and Microengineering, 2008, #18, 7 pgs.

PCT International Search Report, Jul. 8, 2010, 4 pgs.

\* cited by examiner

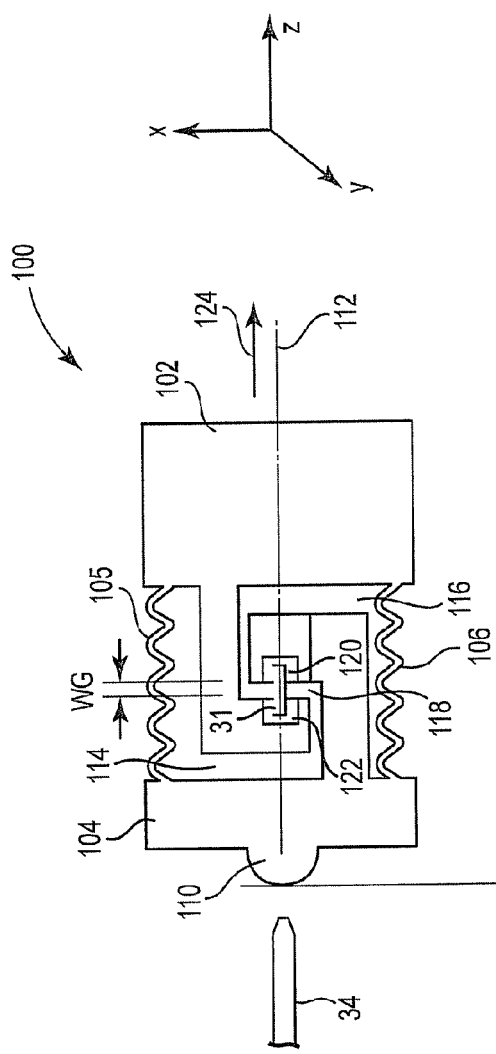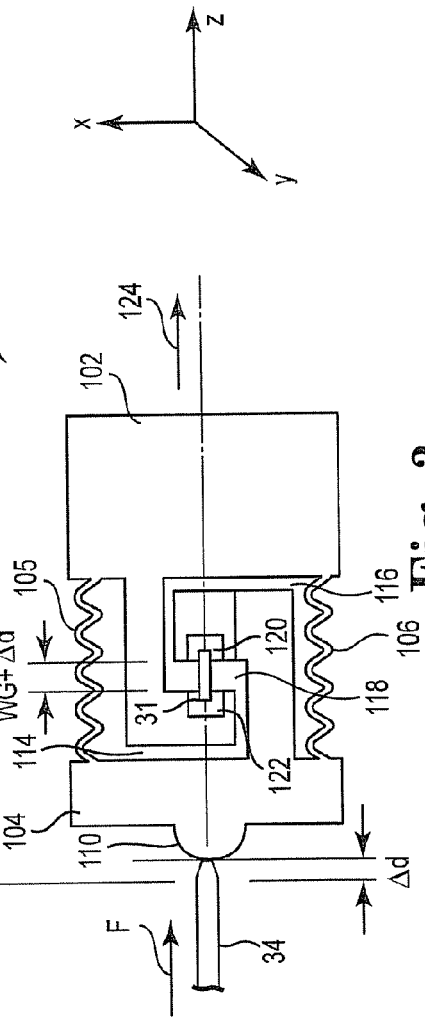

MICRO/NANO-MECHANICAL TEST SYSTEM EMPLOYING TENSILE TEST HOLDER WITH PUSH-TO-PULL TRANSFORMER

CROSS-REFERENCE TO RELATED APPLICATIONS

This Utility Patent application is a continuation of U.S. patent application Ser. No. 12/575,368, filed Oct. 7, 2009 and claims the benefit of U.S. provisional application No. 61/103,456 filed Oct. 7, 2008, both of which are incorporated herein by reference in its entirety.

GOVERNMENT CONTRACT

This invention was made with U.S. Government support under Contract No. DE-FG02-07ER84813, awarded by the Department of Energy. The U.S. Government has certain rights in this invention.

BACKGROUND

The mechanical properties of nanostructures and thin films are important in a number of potential applications such as memory devices, mass sensors, electrochemical transistors, oscillators and nanogenerators. However, measuring the mechanical properties of nanostructures and thin films is difficult for a variety of reasons. First, the mechanical properties of nanostructures cannot be extrapolated from bulk values. Material properties are partly dictated by their physical dimensions, notably the increased surface-to-volume ratio for small volumes. Material properties are also affected significantly by fabrication processes and are sensitive to the influence of interfaces and adjoining materials.

Also, due to their small physical dimensions, the well-established testing techniques used for evaluating the properties of bulk materials are inadequate for nanostructures. Tensile and creep testing of fiber-like materials require that the size of the sample be sufficiently large to be clamped rigidly by a sample holder without sliding. Such an approach is not applicable to nanostructures. Similarly, optical measurements commonly used to evaluate microelectromechanical systems (MEMS) are not valid for measuring the mechanical properties of individual nanowires because the diameters of nanowires are less than the wavelength of visible light. Additionally, the ultra-small size of the nanostructures makes their manipulation difficult and specialized techniques are necessary to pick up and weld individual nanostructures. Therefore, new methods and methodologies have to be developed to quantify the properties of those nanostructures.

In attempts to address these issues, various techniques have been developed to measure the properties of nanostructures. Among them, scanning probe microscopy techniques have been proven to be applicable approaches. One of the first studies regarding scanning probe microscopy measurement techniques was performed by Wong et al. These experiments provide experimental evidence that the mechanical properties of nanostructures may be inherently different from that of their bulk form. However, the experimental measurements have uncertainties, such as precise measurements of the thermal vibrational amplitudes, the effect of a measurement probe tip on the nanostructures, the magnitude of a friction force between the nanostructure and its substrate during bending, and calibration of a probe cantilever. In addition, the experiments did not provide information about the morphologies of stressed nanostructures or on the possible presence and/or evolution of defects trapped inside of the nanostructures.

Due to intrinsically simple geometry, quantitative uniaxial tensile tests on nanostructures have also attracted considerable attention from both theorists and experimentalists. Unlike experimental studies, in which a top-down approach is employed, computer simulations adopt a bottom-up approach to study the mechanical behavior of nanostructures. Such computer simulations have revealed several unexpected physical phenomenon including: (1) ultrahigh elastic strain and, therefore, ultrahigh yield stress; (2) crystalline-to-amorphous transitions; (3) increasing Young's modulus with decreasing cross-sectional area; and (4) crystal structure transition accompanying dramatic changes in Young's modulus. However, without experimental verification, such computer simulations should be regarded only as a source of inspiration and qualitative guidance.

With the high spatial resolution provided by transmission electron microcopy (TEM) and the small probed volume, a quantitative TEM tensile test apparatus provides an experimental means to directly measure the mechanical properties of nanostructures and thin films. Moreover, a quantitative TEM tensile test apparatus provides an opportunity to fill the gap between experiments and simulation. Also, in comparison to other quantitative TEM deformation techniques, such as the quantitative TEM indentation devices developed by Hysitron Inc., for example, TEM tensile tests take advantage of a simple geometry and, as a result, provide experimental results that are relatively easy to explain. A quantitative TEM tensile test device can measure elongation properties of thin films and can reveal the unique deformation mechanisms of nano crystalline materials, which are known to have asymmetrical responses for compression and tensile tests.

Despite great promise, only a few TEM tensile test apparatuses are commercially available, none of which are truly quantitative. As qualitative investigation tools, products such as the TEM tensile holder from Gatan, Inc. can provide physical insight into how materials respond to an applied stress. However, the Gatan holder has several drawbacks which limit its application. First, a force sensor is not available. Second, although equipped with a digital reader for displacement at a micrometer resolution, a manually controlled motorized drive makes it extremely difficult to control the strain rate. Additionally, the Gatan holder has a minimum displacement step at the micrometer level, which makes it difficult to record clear images when shifting a sample from its original position. Also, the Gatan holder design requires at least two steps for sample preparation, the first of which being to make the area of interest of the sample electron transparent, and the second being to mechanically fix the sample to the holder. For thin film or high aspect ratio nanostructures, premature specimen failure during transfer and mounting often makes the test difficult. As such, a tensile test holder design including integrated force and displacement sensors and requiring only single-location sample preparation is desirable.

Some in-situ TEM tensile test holders have been developed by academic researchers. For example, a MEMS-based in-situ TEM tensile tester uses spring displacement to estimate applied force. Although the design provides encouraging information for the development of quantitative TEM nano-mechanical testing, it does not allow recording of an applied force in realtime since the displacement measurement is based on an associated TEM image. The TEM image must also include the displacement measurement structure which adversely affects high resolution sample imaging due to its requirement of a large field of view.

Another device includes two types of actuators: a comb drive electrostatic actuator, which is force controlled, and an in-plane thermal actuator, which is displacement controlled. The Zhu and Espinosa device is capable of applying and measuring load independent of imaging. However, the approach directly welds samples rigidly to the sensor. Considering the practical difficulty in cleaning the residual parts after the test, a new sensor may be required after each test. Furthermore, although chips can be fabricated in large quantities, the calibration, especially with high accuracy and precision, can be difficult.

SUMMARY

One embodiment provides a micromachined or microelectromechanical system (MEMS) based push-to-pull mechanical transformer for tensile testing of micro-to-nanometer scale material samples including a first structure and a second structure. The second structure is coupled to the first structure by at least one flexible element that enables the second structure to be moveable relative to the first structure, wherein the second structure is disposed relative to the first structure so as to form a pulling gap between the first and second structures such that when an external pushing force is applied to and pushes the second structure in a tensile extension direction a width of the pulling gap increases so as to apply a tensile force to a test sample mounted across the pulling gap between a first sample mounting area on the first structure and a second sample mounting area on the second structure.

BRIEF DESCRIPTION OF THE DRAWINGS

FIG. 2 is a schematic diagram generally illustrating a PTP linear mechanical transformer, according to one embodiment.

FIG. 3 is a schematic diagram generally illustrating a PTP linear mechanical transformer, according to one embodiment.

DETAILED DESCRIPTION

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

According to embodiments described herein, a system and method are provided for tensile testing small test samples, such as nanostructures and thin films, to determine the mechanical properties thereof. According to one embodiment, as will be described in greater detail herein, the system includes a micromachined or microelectromechanical (MEMS) based push-to-pull linear mechanical transformer which converts an external pushing force into a tensile force on a material specimen mounted thereto, and enables the use of a nanomechanical test instrument, such as a nanoindenter, for example, which provides a high precision actuation force and high resolution displacement sensing.

Figure 1:
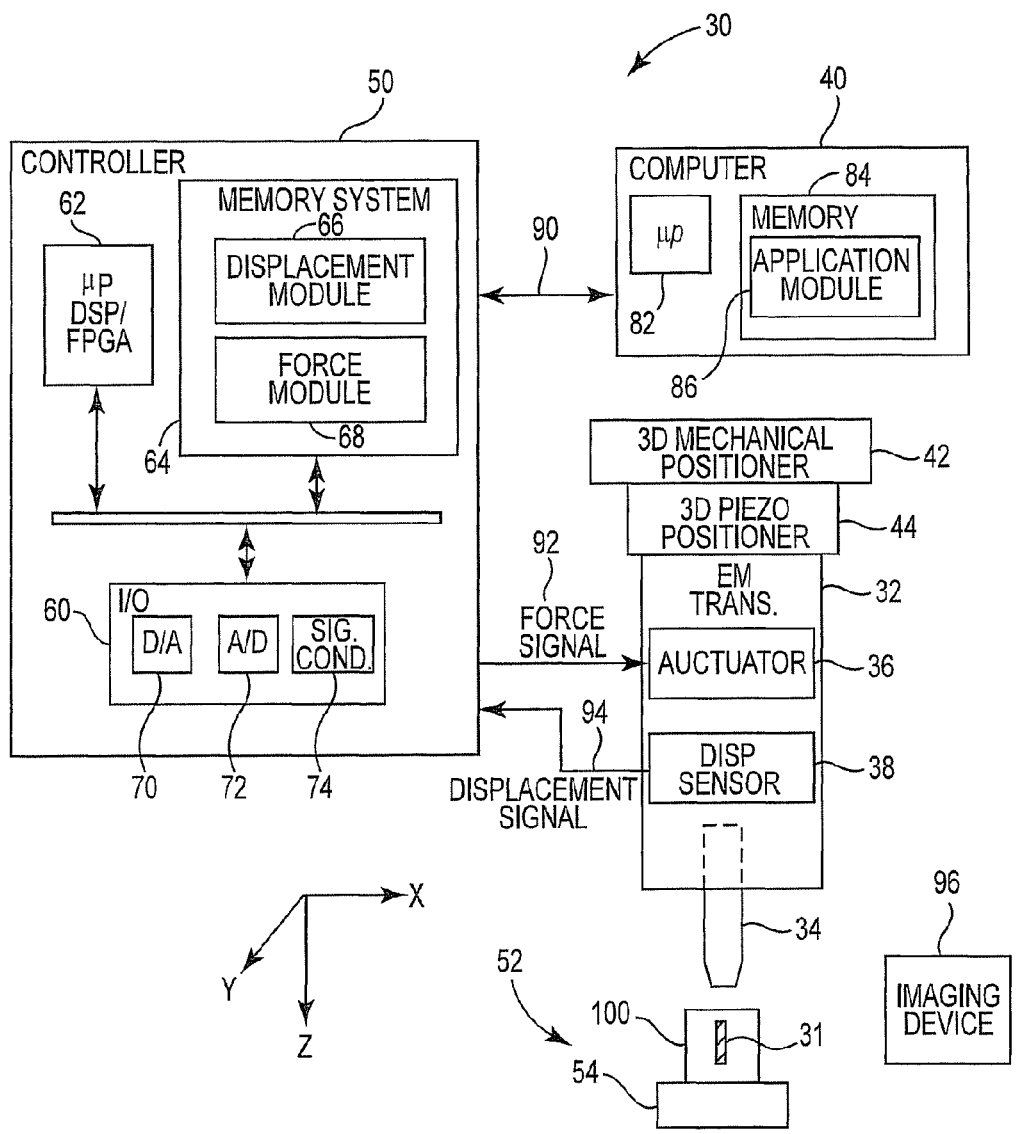
FIG. 1 is a block and schematic diagram generally illustrating a nanomechanical test system employing a push-to-pull (PTP) linear mechanical transformer, according to one embodiment.

FIG. 1 is a block and schematic diagram generally illustrating an example of a nanomechanical test system 30 employing a push-to-pull (PTP) linear mechanical transformer 100 (referred to hereafter as PTP transformer 100) for holding and enabling tensile testing of small test samples (e.g. individual nanowires), such as test sample 31, according to embodiments of the present disclosure. In addition to PTP transformer 100, nanomechanical test system 30 includes an electromechanical (EM) transducer 32 having a displaceable probe 34, an actuator 36, and a displacement sensor 38, a computer 40, a mechanical positioner 42, a piezo positioner 44, a controller 50, and a tensile test holder 52 having a base portion 54 in which PTP transformer 100 is detachably mounted. According to one embodiment, as will be described in greater detail below, tensile test holder 52, including base portion 54 and PTP transformer 100 is micromachined or MEMS based so as to fit into a small, restricted space such as for a quantitative transmission electron microscopy (TEM) in-situ nanomechanical testing application, for example.

According to one embodiment, controller 50 includes an input/output module 60, a processor 62, such as a microprocessor or digital signal processor (DSP) and/or field programmable gate array (FPGA), for example, and a memory system 64. According to one embodiment, memory system 64 includes a displacement module 66 and a force module 68. According to one embodiment, input/output module 60 further includes a D/A converter 70, an A/D converter 72, and a signal conditioner 74.

According to one embodiment, computer 40 includes a processor 82 and a memory system 84 storing an application module 86. Computer 40 may access and communicate with controller 50 via an interface 90 (e.g. a USB interface). Although illustrated in FIG. 1 as comprising separate entities, it is noted that, in other embodiments, computer 40 and controller 50 may be combined as part of a single processing or control system.

According to one embodiment, application module 86, displacement module 66, and force module 68 each comprise instructions respectively stored in memories 64 and 84 and which are accessible and executable by processor 62. Memories 64 and 84 may comprise any number of types of volatile or non-volatile storage devices such as RAM, hard disk drives, CD-ROM drives, and DVD drives, for example. In other embodiments, displacement module 66 and force module 68 may comprise any combination of hardware and software components configured to perform functions described herein. The software component of displacement module 66 and force module 68 may each be stored on a medium separate from processing system 62 prior to being stored in memory system 64. Examples of such a medium include a hard disk drive, a compact disc (e.g. a CD-ROM, CD-R, or CD-RW), and a digital video disc (e.g. a DVD, DVD-R, or DVD-RW), for example.

According to one embodiment, mechanical positioner 42 and piezo positioner 44 enable 3-dimensional positioning (i.e. x-, y-, and z-axes in FIG. 1) of EM transducer 32 and displaceable probe 34 in the millimeter range, but at a sub-nanometer resolution. According to one embodiment, final positioning and movement of displaceable probe 34 is performed by actuator 36 via application module 86 on computer 40 and controller 50. According to one embodiment, controller 50 is configured to control and monitor the movement of displaceable probe 34 and to provide data representative of a displacement of displaceable probe 34 to computer 40 via interface 90. According to one embodiment, controller 50 is configured to determine and adjust a force applied to PTP transformer 100 by displaceable probe 34.

In operation, a user can program controller 50 with computer 40 via application module 86. According to one embodiment, controller 50, via force module 68, provides to actuator 36 an input or force signal 92 representative of a force desired to be applied to tensile test holder 52 by displaceable probe 34. In response to force signal 92, actuator 34 drives displaceable probe 34 toward tensile test holder 52 (e.g. along the z-axis in FIG. 1) such that displaceable probe 34 contacts and applies the desired force to PTP transformer 100. D/A converter 70 converts the input or force signal provided by force module 68 from digital to analog form which, in turn, is amplified by signal conditioner 74 to generate force signal 92 as provided to actuator 36.

Displacement sensor 38 comprises a transducer (e.g. a capacitive transducer) which detects movement of displaceable probe 34 at least along the z-axis, and provides a displacement signal 94 to controller 50 which is representative of such movement of displaceable probe 34. In other embodiments, in addition to movement along the z-axis, displacement sensor 38 detects and provides indication of other types of movement of displaceable probe 34, such as displacement along the x- and/or y-axes or rotational movement about the x- and/or y-axes, for example. Signal conditioner 74 extracts the desired range of signals from the displacement signal 38. A/D converter 72 converts displacement signal 94 from an analog form, as received from displacement sensor 38, to a digital form for processing by displacement module 66 which, according to one embodiment, provides indication of the movement of displaceable probe 34 to force module 68 (e.g. for force calculations) and computer 40 (via interface 90).

According to one embodiment, controller 50 is further configured to control movement or displacement of displaceable probe 34 in the x- and y-directions relative to tensile test holder 52, such as by moving EM transducer 32 relative to tensile test holder 52 or by moving tensile test holder 52 relative to EM transducer 32 (e.g. by moving tensile test holder 52). According to one embodiment, nanomechanical test system 30 further includes an imaging device 96 comprising an instrument/device such as an optical microscope or a scanning probe microscope (SPM) (e.g., an atomic force microscope (AFM)) configured to provide images of a test sample mounted to tensile test holder 52.

Examples of nanomechanical test systems suitable to be configured for use with a tensile test holder according to embodiments of the present disclosure are described by U.S. Pat. Nos. 5,553,486 and 5,869,751, both of which are assigned to the same assignee as the present disclosure and incorporated herein by reference. Another test system suitable to be configured for use with the PTP transformer 100 of the present disclosure is an electron microscopy (e.g. transmission electron microscopy and/or scanning electron microscopy) in-situ nanomechanical tester commercially available under the tradename PicoIndenter from Hysitron, Incorporated, of Minneapolis, Minn., USA.

During a tensile testing operation, as will be described in greater detail below, EM transducer 32 is controlled so as to apply a pushing force with displaceable probe 34 to PTP transformer 100 which, in-turn, transforms the pushing force to a pulling force which is applied to a test sample 31, such as a nanowire, for example. According to one embodiment, the force applied to and a displacement of test sample 31 are measured by nanomechanical test system 30 via actuator 36 and displacement sensor 38 of EM transducer 32 while being synchronously imaged via imaging device 96.

FIG. 2 is a schematic diagram generally illustrating PTP transformer 100, according to one embodiment. As illustrated, PTP transformer 100 includes a first or stationary structure 102 which, according to one embodiment, mounts to base portion 54 (see FIG. 1), and a second or moveable structure 104 which is coupled to stationary structure 102 via at least one spring, and illustrated as being coupled to stationary structure 102 by two springs, springs 105 and 106, in the embodiment of FIG. 2. In other embodiments, as will be described below, more than two springs may be employed. Moveable structure 104 further includes a contact head 110 to which an external actuator, such as displaceable probe 34 of EM transducer 32, applies a pushing force to displace moveable structure 104.

According to one embodiment, stationary structure 102 and moveable structure 104 are shaped so as to form a pair of pushing gaps 114 and 116 and a pulling gap 118 between moveable structure 104 and stationary structure 102, with pulling gap 118 being positioned between pushing gaps 114, 116, and pushing gaps 114, 116 and pulling gap 118 each crossing a force or actuation axis 112 along which a pushing force is applied, such as by EM transducer 32. According to one embodiment, as illustrated, the force or actuation axis comprises centerline 112 of PTP transformer 100. According to one embodiment, pushing gaps 114, 116 and pulling gap 118 are each substantially perpendicular to centerline 112. Sample mounting areas 120 and 122 are positioned on opposite sides of pulling gap 118, with sample mounting area 120 being positioned on moveable structure 104 and sample mounting area 122 being positioned on stationary structure 102.

When in a relaxed state (i.e. no pushing force is being applied to moveable structure 104), as illustrated by FIG. 2, springs 105 and 106 are not compressed or deflected, and pulling gap 118 has a width $W_G$ across which test sample 31 is mounted. According to one embodiment, width $W_G$ is narrow enough to enable mounting of high aspect ratio nanostructures across pulling gap 118 between sample mounting areas 120 and 122, but wide enough to enable an electron beam to pass through for TEM imaging purposes. According to one embodiment, pulling gap 118 has a width $W_G$ of approximate 4 μm. In FIG. 2, test sample 31 (e.g. a nanowire) is illustrated as being mounted across pulling gap 118 and secured to sample mounting areas 120, 122. As described below, test sample 31 may be secured to sample mounting areas 120, 122 via a welding process, for example, which is described in greater detail below. According to one embodiment, to achieve the most accurate tensile measurements, test sample 31 is aligned with the pushing force axis which, in this case, comprises centerline 112.

During a tensile testing operation, as illustrated by FIG. 3, an actuator, such as displaceable probe 34 of EM transducer 32 applies a force to and pushes moveable structure 104 in a tensile extension direction 124. According to one embodiment, a tip of displaceable probe 34 is positioned so as to moveable structure 104 at contact head 110 and apply a pushing force F to moveable structure 104 in tensile extension direction 124. To achieve the most accurate tensile measurements, pushing force F should be aligned with centerline 112 in order to reduce the potential for rotational movement of moveable structure 104 that might result from misalignment. In this regard, the semicircular or half-moon shape and symmetrical positioning of contact head 104 about centerline 112 helps to ensure the alignment of pushing force F with centerline 112 as only a top portion of contact head 110, which is aligned with centerline 112, is able to be contacted by displaceable probe 34. According to one embodiment, displaceable probe 34 comprises a flat punch configuration which achieves a contact point along centerline 112 with contact head 110.

As displaceable probe 34 pushes moveable structure 104 in tensile extension direction 124, springs 105 and 106 compress or deflect and pushing gaps 114, 116 become narrower while pulling gap 118 widens or extends in tensile direction 124 and begins to stretch or elongate test sample 31 until, ultimately, test sample 31 fractures or fails. According to one embodiment, as will be described in greater detail below, springs 105, 106 are configured so as to be readily deflectable in the tensile extension direction 124, but to be substantially rigid in directions other than tensile extension direction 124. Due to this configuration of springs 105 and 106, and to a rigidity of moveable structure 104, moveable structure 104 moves only along centerline 112 (i.e. only along the z-axis) so that it can be assumed that the distance that pulling gap 118 widens or extends is equal to the displacement, Δd, of displaceable probe 34 as measured by nanomechanical test system 30 based on displacement signals 94 provided by displacement sensor 38 (see FIG. 1).

In addition to measuring the displacement or elongation of test sample 31, nanomechanical test system 30 measures the force or load applied to test sample 31 as it stretches or elongates. According to one embodiment, the force or load applied to test sample 31 is equal to the force measured by nanomechanical test system 30 via EM transducer 32 minus known force-displacement characteristics of PTP transformer 100, which are measured when no sample is mounted thereto (see FIGS. 7-9 below) or is measured after failure of the sample using the force-displacement curve when no force contribution from the sample is present. Simultaneously and synchronously with the application of pushing force F by displaceable probe 31, images are obtained of test sample 31 by imaging device 96. From the force/displacement measurements and images provided by nanomechanical test system 30, the tensile characteristics (e.g. Young's modulus) can be determined.

According to one embodiment, because of the single axis movement of moveable structure 100 (i.e. along centerline 112), the fractured surfaces of test sample 31 will match to one another after retracting of the external pushing force F by EM transducer 32 and contraction of springs 105, 106. By once again applying a pushing force F to contact head 110 to again separate fractured test sample 31, an attraction force and distance between the fractured surfaces of failed test sample 31 can be measured.

Figure 4:
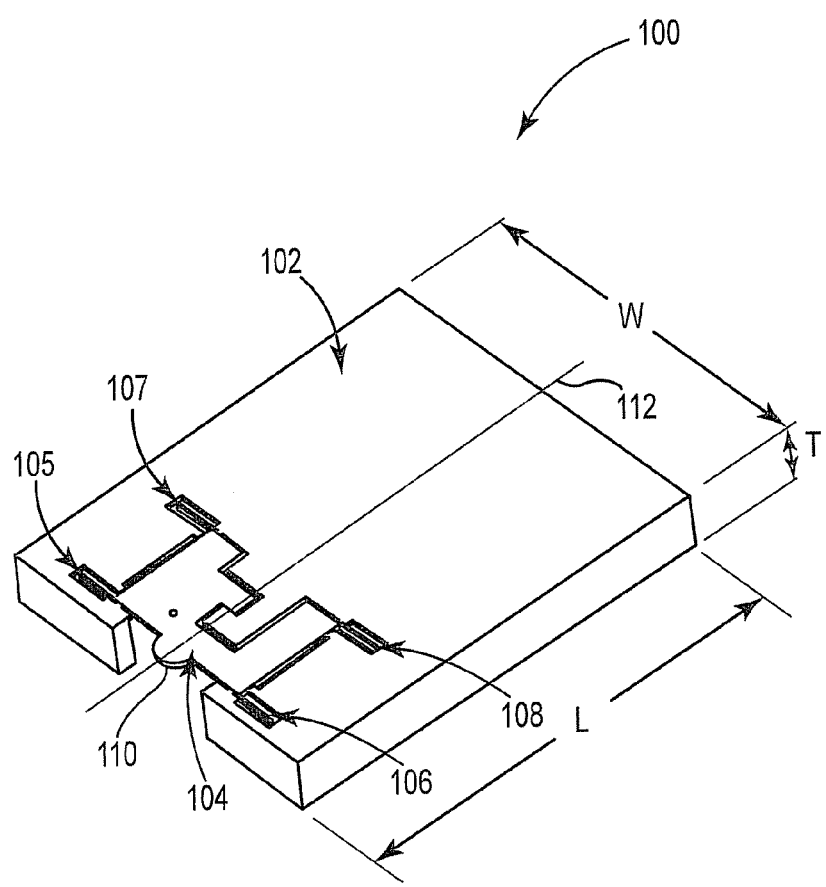
FIG. 4 is a perspective view illustrating a PTP linear mechanical transformer according to one embodiment.

FIG. 4 is a perspective view illustrating PTP transformer 100, according to one embodiment, wherein four springs are employed to couple moveable structure 104 to stationary structure 102. Accordingly, in addition to springs 105 and 106, as illustrated by FIGS. 2 and 3, the embodiment of PTP transformer 100 of FIG. 4 additionally employs springs 107 and 108. According to one embodiment, as illustrated by FIG. 4, springs 105, 106, 107, and 108 are positioned at the corners of moveable structure 104. It is noted that, as compared to the two-spring embodiment of PTP transformer 100 illustrated in FIGS. 2 and 3, the embodiment of PTP transformer 100 of FIG. 4 employing four springs 105, 106, 107, 108 reduces the potential for distortion of sample mounting area 120 on movable structure 104 relative to sample mounting area 122 on stationary structure 102 which might otherwise be caused by gravitational forces on movable structure 104. As a result, the four-spring embodiment of PTP transformer 100 of FIG. 4 provides a more stable linear motion of movable structure 104 during a tensile testing procedure as compared to the two-spring embodiment of FIGS. 2 and 3.

It is noted that the pushing force, F, can be applied to PTP transformer 100 in several ways. For example according to one embodiment, the force can be applied using EM transducer 32 under open-loop or closed-loop control and is applied in a fashion so as to execute a predefined load function. According to another embodiment, the force can be applied by EM transducer 32 under closed-loop displacement control so as to execute a predefined displacement function. According to another embodiment, EM transducer 32 can apply the force with periodic oscillation, under open-loop or closed-loop control, so as to determine dynamic characteristics of test sample 31.

As illustrated, PTP transformer has a length (L), a width (W), and a thickness (T). According to one embodiment, PTP transformer 100 is micromachined so as to be able to accommodate micrometer-to-nanometer scale test specimens and to be able to fit within the restricted spaces required by some nanomechanical applications, such as for in-situ TEM mechanical testing, for example. For example, the maximum allowable thickness (T) and width (W) for Technai $G^2$ TEM type holders is 2 mm and 4 mm, respectively. According to one embodiment, PTP transformer 100 has a length (L) of 3 mm, a width (W) of 2.5 mm, and a thickness (T) of 0.4 mm.

Figure 5:
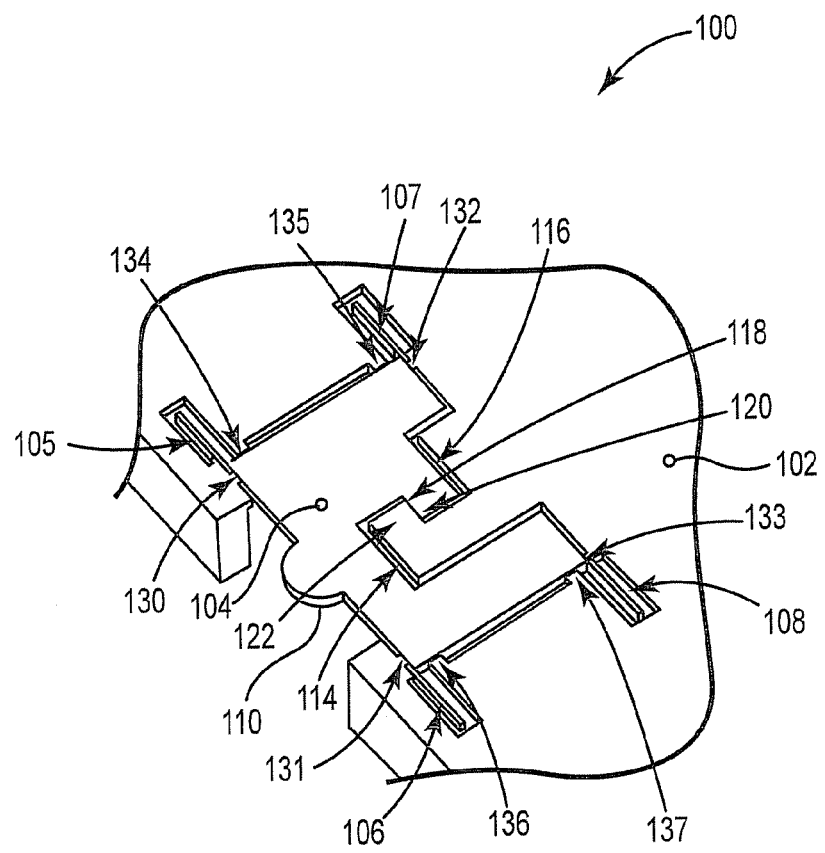
FIG. 5 is an enlarged view of a portion of the PTP linear mechanical transformer of FIG. 4.

FIG. 5 is an enlarged perspective view illustrating portions of PTP transformer 100 of FIG. 4. As illustrated, stationary structure 102 includes a plurality of motion limiter structures 130-137 which extend from stationary structure 102 around perimeter edges of movable structure 104 and restrict the motion of moveable structure 104 so as to prevent damage to PTP transformer 100 which could otherwise be caused by excessive deformation of springs 105-108. Motion limiters 130, 131 are positioned along a front edge of moveable structure 104, motion limiters 132, 133 are positioned along a rear edge of moveable structure 104, and motion limiters 134, 135 and 136, 137 are positioned on opposing side edges of moveable structure 104.

As motion limiters 130-137 extend from stationary structure 102, moveable structure 104 contacts only the surfaces of motion limiters 130-137, which are small relative to the surface areas of the larger side walls of stationary structure 102. The small contact area results in any stiction force between moveable structure 104 and the motion limiters being smaller that the spring reaction of springs 105-108 such that moveable structure 104 will move away from motion limiters 130-137 and return back to a normal movement position by the spring reaction. According to one embodiment, contact between moveable structure 104 and motion limiters 130-137 does not result in damage because a maximum stress from displacement of moveable structure 104 within the area of motion defined by motion limiters 130-137 is less than a yield strength of a material from which moveable structure 104 and motion limiters 130-137 are formed (e.g. single crystal silicon).

Figure 6:
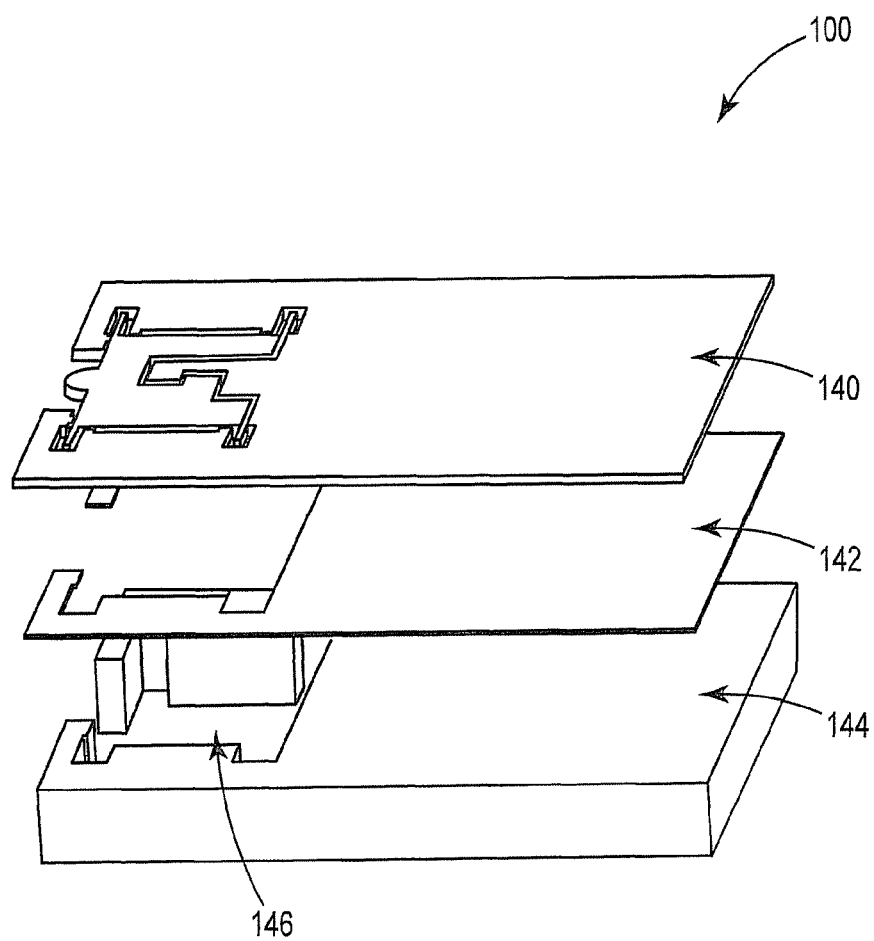
FIG. 6 is an exploded view of the PTP linear mechanical transformer of FIG. 4.

FIG. 6 is an exploded view of PTP transformer 100 of FIGS. 4 and 5. According to one embodiment, as illustrated, MEMS-based PTP transformer is formed via micromachining techniques from three layers: a device layer 140, an etch stop layer 142, and a substrate 144. According to one embodiment, moveable structure 104, including contact head 110, springs 105-108, and motion limiters 130-137 are fabricated on device layer 140 using photolithographic and etching processes, such as deep reactive ion etching (DRIE) techniques. Etch stop layer 142 which, according to one embodiment, comprises a silicon dioxide layer, is disposed between device layer 140 and substrate 144. According to one embodiment, substrate 144 is deep-etched to form an open area 146 to expose moveable structure 104 and springs 105-108.

According to one embodiment, PTP transformer 100 is micromachined from a silicon-on-insulator (SOI) wafer. According to one embodiment, to achieve high electrical conductivity, heavily boron doped p-type silicon wafers were used for the device layer 140 and substrate 144. According to one embodiment, an electrical resistivity of the SOI wafer was in a range of 0.005-0.02 ohm-cm.

Figure 7:
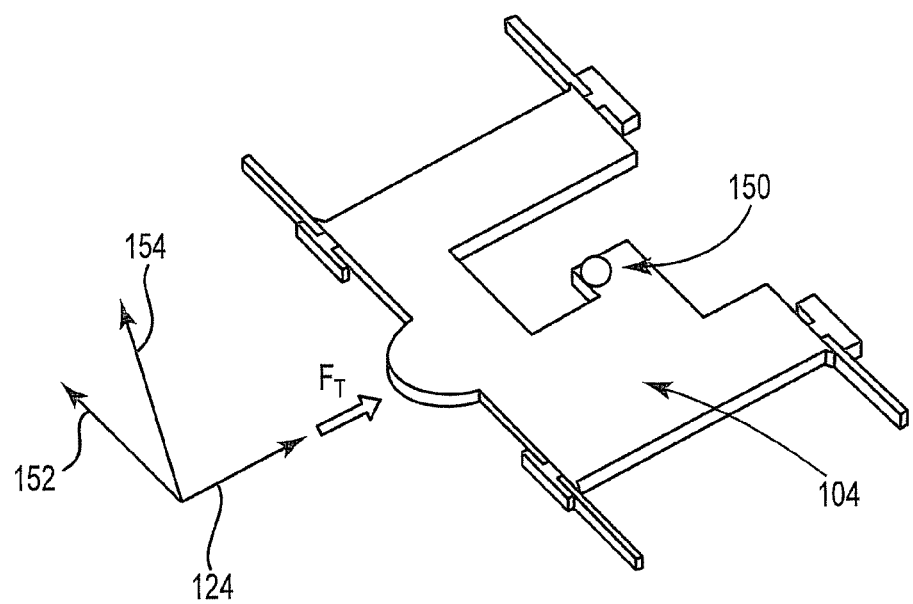
FIG. 7 is a perspective view illustrating a moveable structure of a PTP linear mechanical transformer, according to one embodiment.

A process for fabricating MEMS based PTP linear mechanical transformer 100 using micromachining techniques is briefly described below. The process begins with a starting material which, according to one embodiment, is a heavily boron doped SOI wafer as described above. A silicon dioxide layer is deposited on a backside of substrate 144 and patterned, such as by reactive ion etching (RIE) using a mask (e.g. a photoresist) patterned with the shape and dimensions of opening 146. Next, a mask patterned with moveable structure 104, including contact head 110 and gaps 114, 116, and 118 (as well as other gaps), springs 105-108, and motion limiters 130-137 is formed on device layer 140, and device layer 140 is etched using DRIE processes. Substrate 144 is then etched (e.g. using DRIE) via the patterned oxide layer on the rear side. The silicon dioxide layer on substrate 144 and etch stop layer 142 are then etched by RIE processes. FIG. 7 is a perspective view of moveable portion 104 of PTP transformer 100 of FIG. 4. As described above, in order for a pushing force to be linearly transferred to a pulling or tensile force on a sample, the stiffness of moveable portion 104, in particular springs 105-108, should allow for easy movement of moveable portion 104 in pushing direction 124 while prohibiting movement in directions other than pushing direction 124.

To estimate the static and dynamic characteristics of moveable portion 104 of PTP transformer 100 of FIG. 4, according to one embodiment, three finite element analyses of PTP transformer 100 were performed using the commercially available finite element analysis software COSMOSWorks®. In each of the simulations, springs having a 5-μm thickness were examined and, as boundary conditions, the four side wall faces at an end of a spring were fixed, 50,000 triangular elements were used, and the material property was modeled with an elastic modulus of 120 GPa, a Poisson's ratio of 0.28, a mass density of 2,330 kg/m$^3$, and a yield strength of 7 GPa.

For each of the three analyses, a 100-μN test force ($F_T$) was applied to contact head 110 along centerline 112 and a displacement of a sample mounting point, indicated at 150 in FIG. 7, was estimated. Determining the displacement of sample mounting point 150 provides information as to how a force applied on centerline 112 at contact head 110 affects the tensile testing of PTP transformer 100. While a test force ($F_T$) having a magnitude of 100-μN was used in each of the simulations, the direction of the force was changed each time to estimate the stiffness of moveable structure 104 in operational or tensile extension direction 124, a lateral direction 152, and a vertical direction 154.

In a first simulation, when the 100-μN was applied in operational or tensile extension direction 124, a displacement of probing point 150 was estimated to be 798 nm. Based on this simulation, a stiffness of a PTP transformer 100 in operational or tensile extending direction 124 with a 5-μm spring thickness was estimated to be 125 N/m. In this simulation, the springs 105-108 have a high stress concentration with a maximum stress estimated at 11.9 MPa. This maximum stress is much lower than a 7 GPa yield strength of single crystal silicon and indicates that the PTP transformer 100 will have linear characteristics up to one order larger displacement change such that it would not be damaged by the displacement change.

From the other two simulations, with force directions in the lateral and vertical directions 152 and 154, based on the displacement of sample mounting point 150, the lateral and vertical stiffness of PTP transformer 100 were respectively estimated at 3,890 N/m and 2,150 N/m. The relatively larger lateral and vertical stiffness as compared to the stiffness in operational or tensile extension direction 124 enable the tensile extension to be unidirectional in the operational or tensile extension direction 124. Such a stiffness characteristic substantially eliminates the effects of undesired lateral and vertical force components in a tensile test.

Additionally, the resonant frequency of PTP transformer 100 of FIG. 4 was estimated to be approximately 6.5 kHz. For comparison, in-situ TEM nanoindenter transducers from Hysitron, Inc. have 250 Hz (i.e., transducers designed for JEOL TEMs) and 3.5 kHz (i.e., MEMS transducer) bandwidth. As such, PTP transformer 100 has higher bandwidth as compared to the pushing apparatus, such as EM transducer 32 (see FIG. 1) so that PTP transformer 100 can follow the dynamic inputs from the pushing apparatus. Such a high bandwidth characteristic is especially useful for dynamic tensile testing, as it enables a wide range of operational frequencies for the dynamic tensile test because the measurements will not be affected by the dynamic characteristics of PTP transformer 100.

Figure 8:
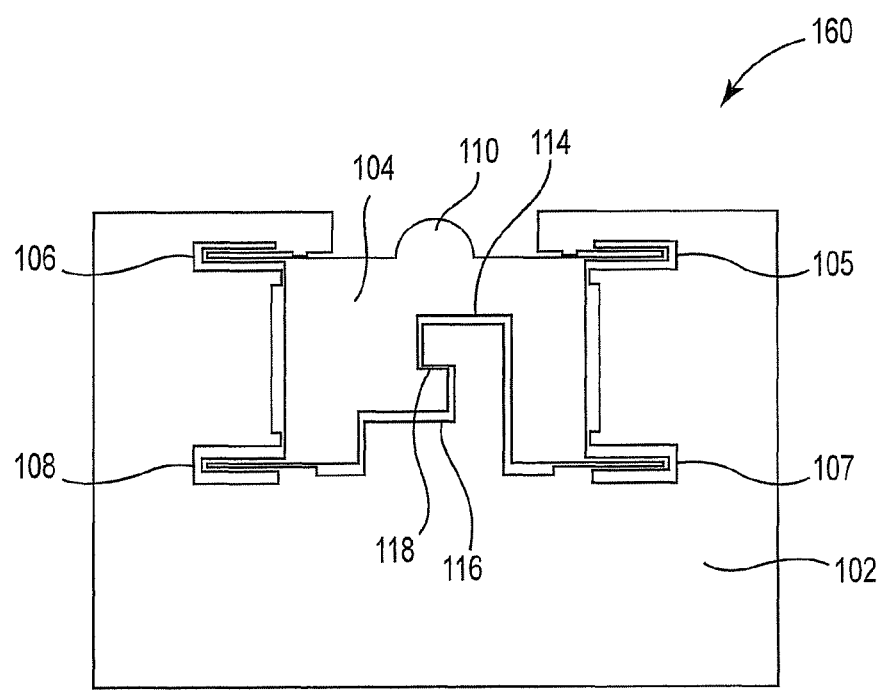
FIG. 8 is an image illustrating an example of a fabricated PTP linear mechanical transformer, according to one embodiment.

FIG. 8 is a microscope image 160 of portions of one embodiment of a fabricated micro-machined PTP transformer 100 similar to that illustrated above by FIG. 4. In image 160, the width of pulling gap 118 is approximately 4 μm and has a nominal length of about 100 micrometers. By changing a thickness of springs 105-108, the stiffness of the PTP transformer 100 can be adjusted to provide force sensitivity and motion stability appropriate for the testing of a variety of test materials of different stiffness.

According to one embodiment, five different PTP transformers 100 were fabricated, each employing a different nominal spring thickness so as to provide each of the PTP transformers 100 with a different stiffness. According to one embodiment, the five different PTP transformers 100 employed springs 105-108 having a nominal spring thicknesses of 4, 5, 6, 7, and 8 μm. Stiffness measurement results showed that a stiffness of the five different PTP transformers 100 ranges from 10 N/m to 400 N/m depending on the spring thickness.

Figure 9:
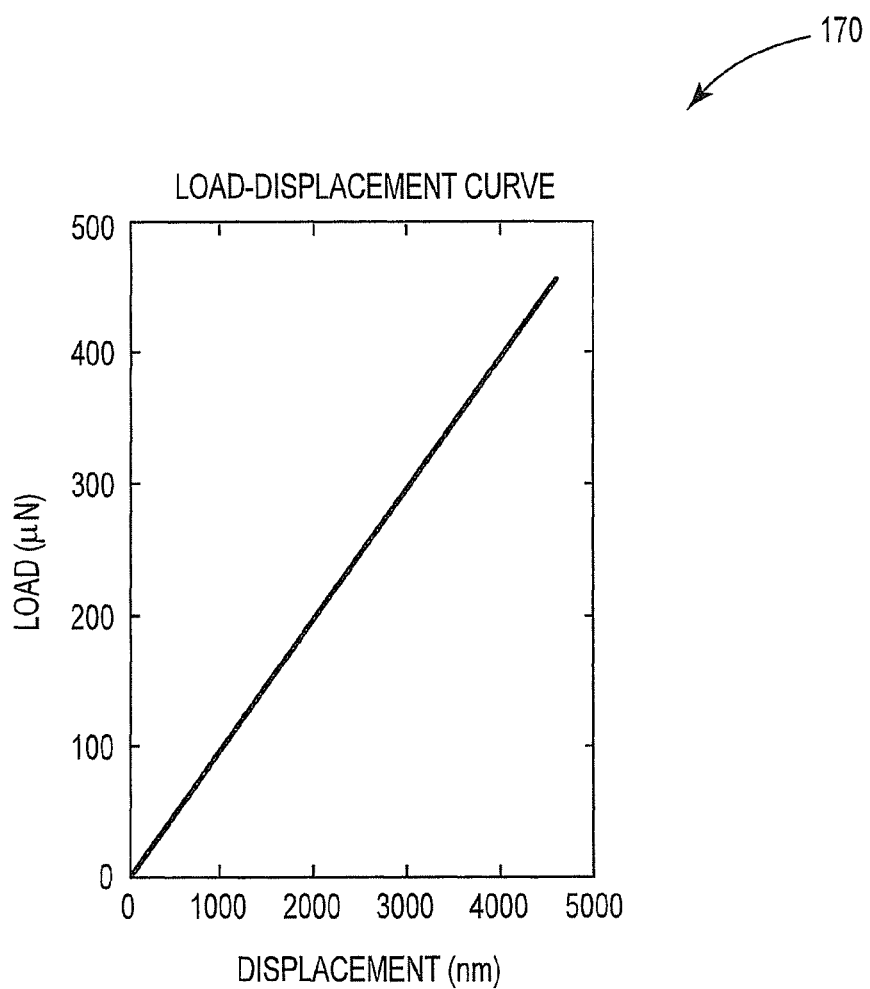
FIG. 9 is an example of a load-displacement curve of a PTP linear mechanical transformer, according to one embodiment.

FIG. 9 illustrates a load-displacement curve 170 of one embodiment of a PTP transformer 100 similar to fabricated example of FIG. 8. From curve 170, it can be seen that there is a linear change in the displacement of moveable structure 104 to the pushing load applied by the actuator, such as displaceable probe 34 of EM transducer 32 (see FIG. 1). From this linear relationship, it easy to calculate a stiffness of the test sample from the data measured by EM transducer 32. The force applied to moveable structure 104 is measured by the pushing apparatus (e.g. EM transducer 32) and the reaction of moveable structure 104 is subtracted from the applied load to estimate the load or force on the test sample. Based on this linear relation, the reaction of moveable structure 104 of PTP transformer 100 is simply calculated using the stiffness and displacement of moveable structure 104. In FIG. 9, the stiffness in the operational or tensile extension direction 124 of PTP transformer 100 represented by curve 170 is seen to be 100 N/m. It is noted that the stiffness of PTP transformer 100 of FIG. 9 was also measured in lateral and vertical directions 152, 154 and were found to be more than 30 times higher than that in tensile extension direction 124.

Figure 10:
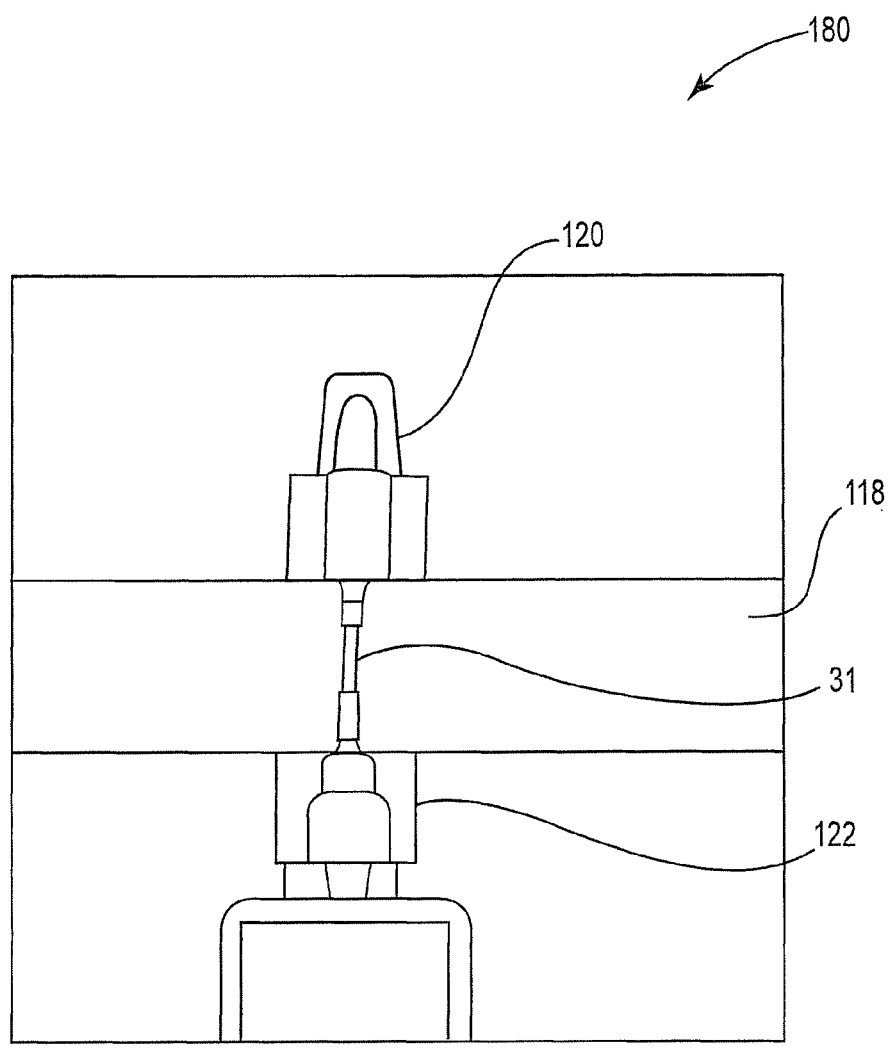
FIG. 10 is an image illustrating an example of a sample mounted on a PTP linear mechanical transformer, according to one embodiment.

FIG. 10 is a scanning electron microscope image 180 illustrating an example of a test sample 31 mounted across pulling gap 118 between sample mounting areas 120 and 122 of PTP transformer 100, according to one embodiment. In image 180, mounted test sample 31 is a silicon nanowire having a length of 20 μm and a diameter of 250 nm.

An example of a process for mounting a single nanowire onto PTP transformer 100 is described briefly below. In the described process, a FEI Strata 235 Dual-Beam Focused Ion Beam (FIB) system by FEI Company was used to mount the sample. According to one embodiment, the mounting process includes:

(1) Gluing PTP transformer 100 to a brass entity or holder, such as base portion 54 of tensile test holder 52, and then transferring tensile test holder 52 into the chamber of the FIB system along with one or more nanowires to be tested. The relative geometry among the nanowires, tensile test holder 52, the electron beam (e-beam), the ion beam (i-beam), and micro/nano-manipulator is a system which enables the handling of nanoscale objects is determined;

(2) Aligning the one or more nanowires with their growth direction perpendicular to the e-beam direction of the FIB using the micro/nano-manipulator, welding the free end of a nanowire sample to be tested to a tungsten tip of the micro/nano-manipulator with the FIB with e-beam assisted Pt deposition, and cutting the nanowires to be tested from its root using a low-current i-beam (30 pA used in this experiment);

(3) Positioning PTP transformer 100 of tensile test holder 52 proximate to the nanowires sample with pulling gap 118 positioned perpendicular to the nanowires sample (in one embodiment, contact of the nanowires sample with PTP transformer 100 was confirmed by slightly tapping the table while simultaneously monitoring the scanning image of the nanowire sample); and (4) Welding the nanowire sample to sample mounting areas 120, 122 across pulling gap 118 of PTP transformer 100 (e.g. via deposition of gold or other metal) and cutting off the nanowire with a low-current ion beam from the micro/nano-manipulator tip. In order to minimize a gauge size so as to improve the chance of identifying initial deformation phenomenon under high magnification, e-beam deposition was used to strengthen the welds at both ends of the nanowire sample.

Figure 11:
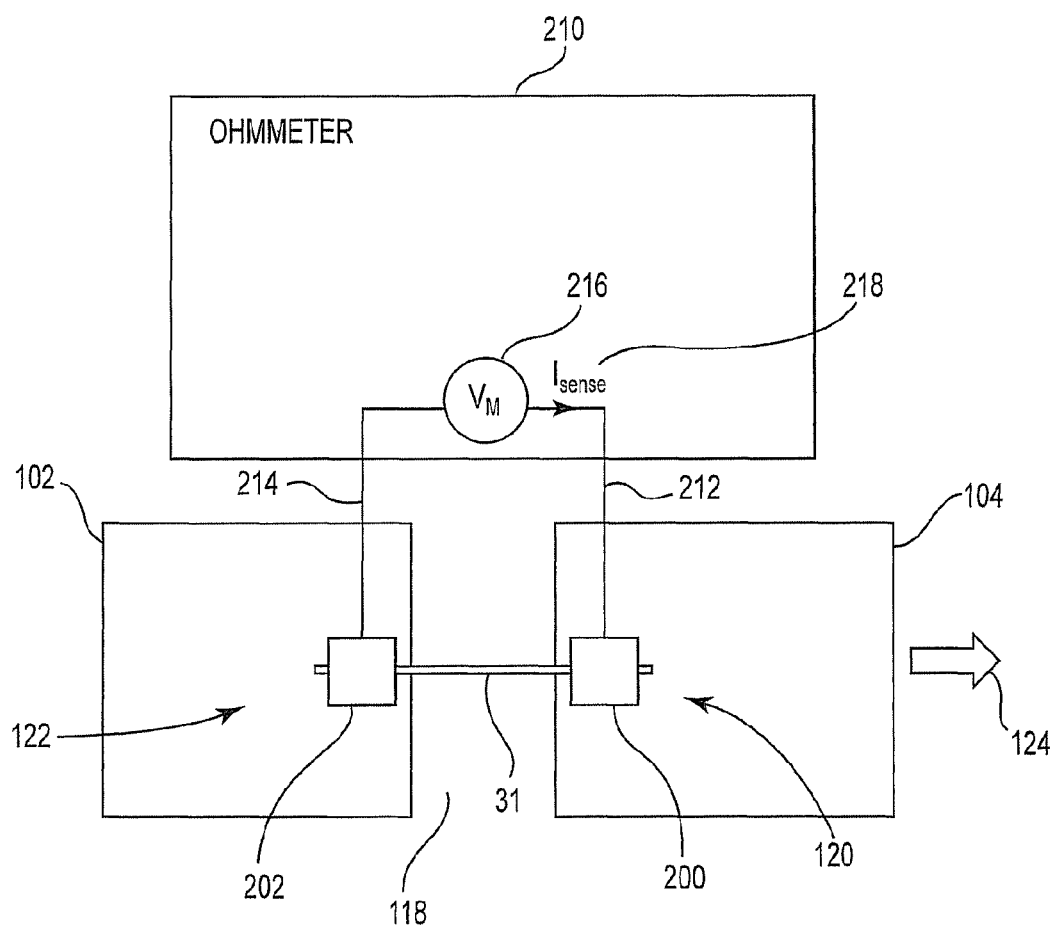
FIG. 11 is a block and schematic diagram of a PTP linear mechanical transformer configured to enable performance of electro-mechanical tensile testing, according to one embodiment.
Figure 13:
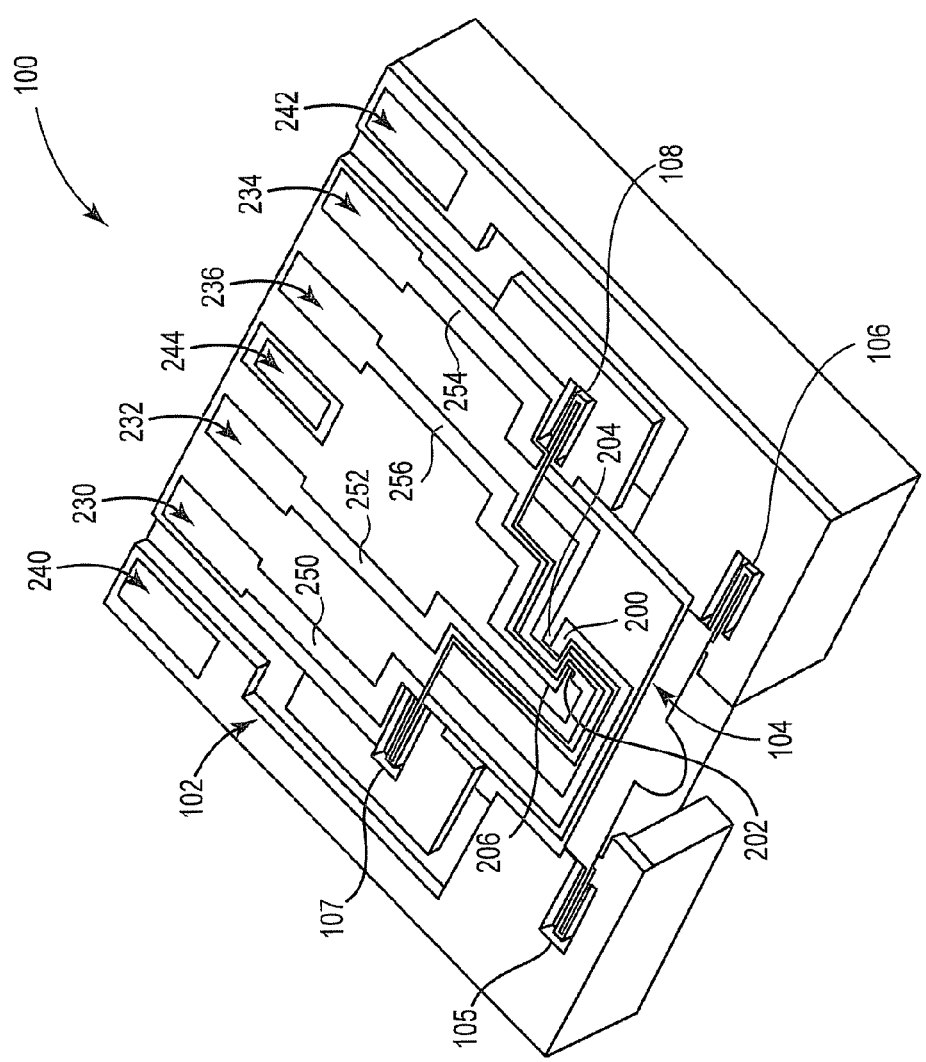
FIG. 13 is a perspective view illustrating the PTP linear mechanical transformer of FIG. 12, according to one embodiment.
Figure 14:
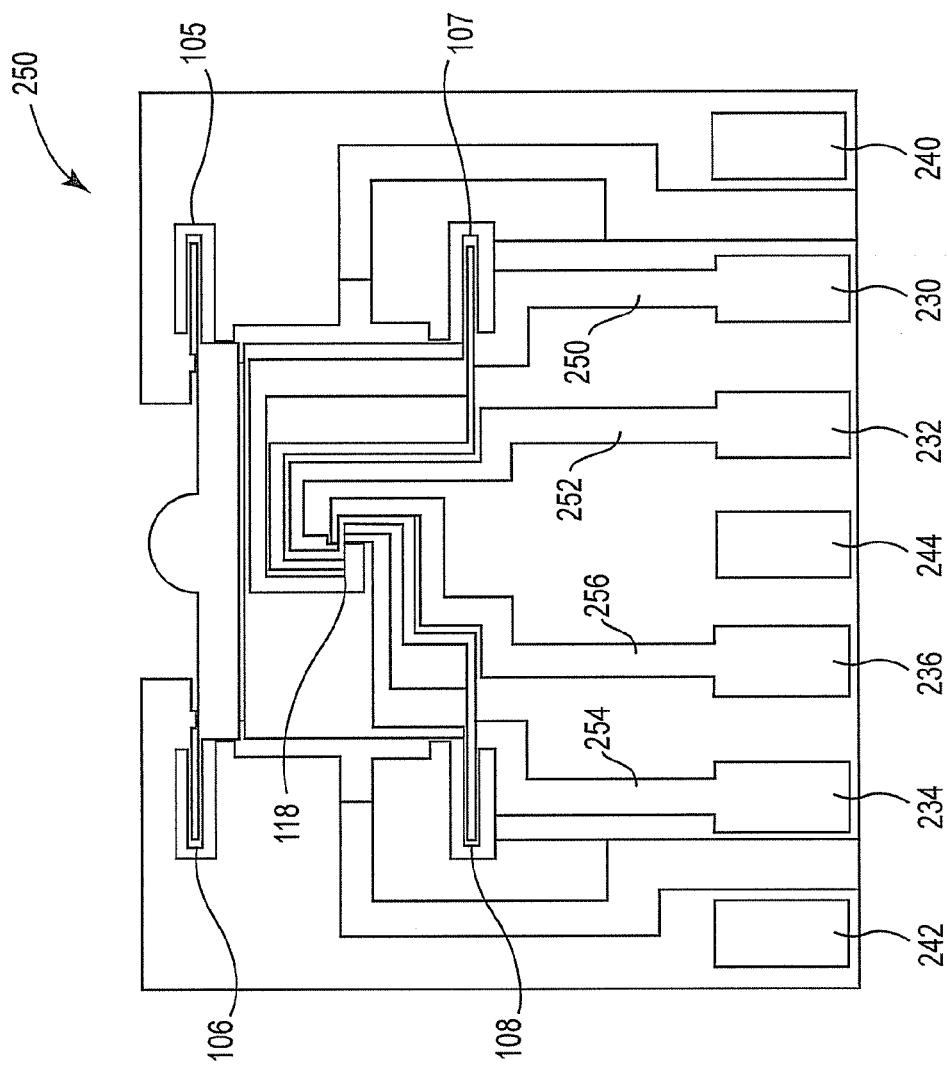
FIG. 14 is an image illustrating a fabricated PTP linear mechanical transformer similar to the PTP linear mechanical transformer of FIG. 13, according to one embodiment.

According to embodiments described below with respect to FIGS. 11 through 15, PTP transformer 100 can be configured to enable electromechanical and thermal-mechanical tensile testing to be performed on a test sample. FIG. 11 is a block and schematic diagram generally illustrating PTP transformer 100, according to one embodiment. A first sample contact 200 is formed (e.g. via metal deposition and photolithographic patterning processes) in sample mounting area 120 of moveable structure 104, and a second sample contact 202 is formed in sample mounting area 122 of stationary structure 102. An external ohmmeter 210 is respectively coupled to first and second sample contacts 200, 202 via leads 212 and 214 (e.g. at least partially comprising conductive traces on stationary and moveable structures 102, 104, as illustrated by FIGS. 13 and 14 below). Test sample 31 is connected to contacts 200, 202, such as by welding processes as described above (e.g. via deposition of gold or other suitable electrically conductive material), across pulling gap 118.

During a tensile testing procedure, a voltmeter 216 of ohmmeter 210 provides a sense current 218 which passes through test sample 31 via contacts 200, 202 and leads 212, 214 to measure an electrical resistance of test sample 31 during the tensile testing procedure. Such a configuration is generally referred to as a two-point measurement. It is noted that, according to such a two-point measurement, the ohmmeter measures not only the resistance across test sample 31, but also that of contacts 200, 202 and leads 212, 214.

Figure 12:
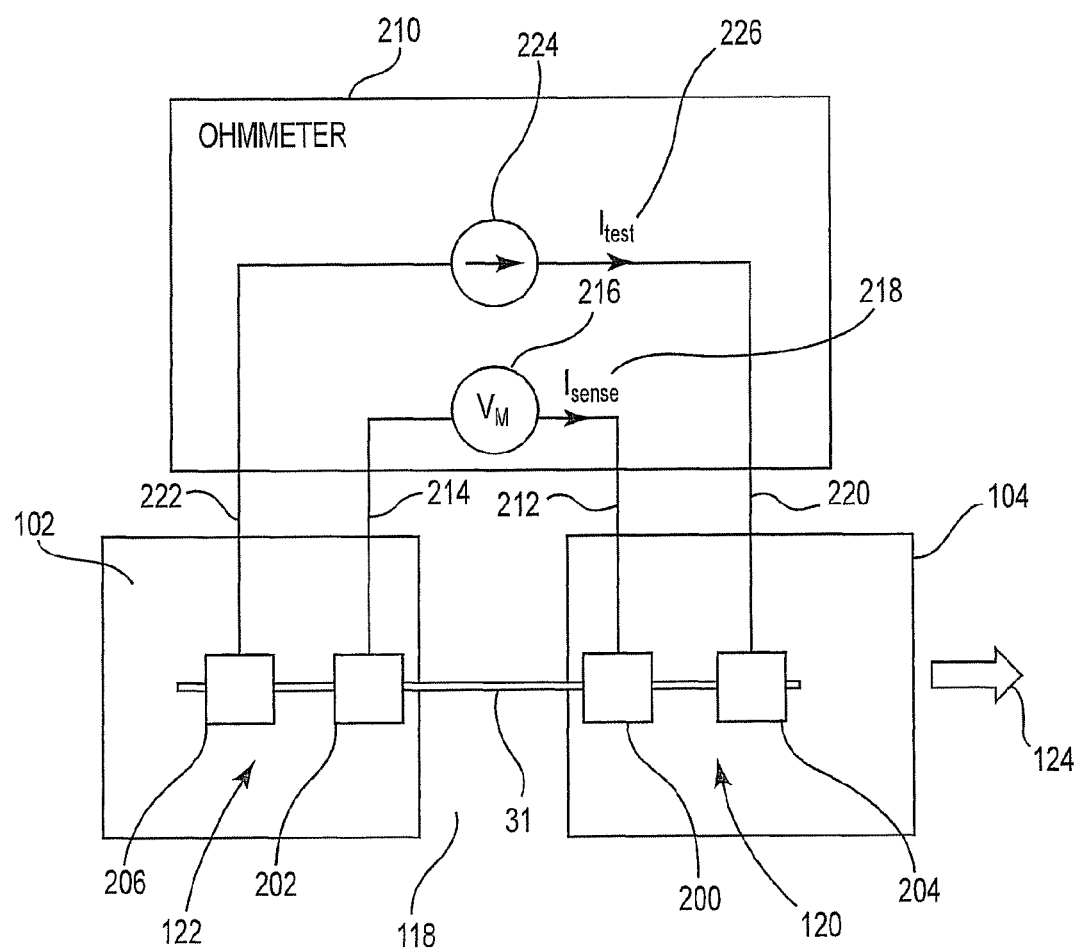
FIG. 12 is a block and schematic diagram of a PTP linear mechanical transformer configured to enable performance of electro-mechanical tensile testing, according to one embodiment.

FIG. 12 is a block and schematic diagram generally illustrating a further embodiment of PTP transformer 100. In addition to first and second sample contacts 200, 202, PTP transformer 100 includes a further contact 204 formed in sample mounting area 120 of moveable structure 104 and a further contact 206 formed in sample mounted area 122 of stationary structure 102. Test sample 31 is connected to contacts 200, 204 of moveable structure 104 and to contacts 202, 206, across pulling gap 118. In addition to leads 212, 214, external ohmmeter 210 is respectively coupled to sample contacts 204 and 206 via leads 220 and 222.

As with the implementation of FIG. 11, during a tensile testing procedure external ohmmeter 210 is respectively coupled to first and second sample contacts 200, 202 via leads 212 and 214 and provides a sense current 218 via voltmeter 216. Additionally, a power supply 224 of ohmmeter 210 is coupled to and provides a test current 226 through sample 31 via contacts 204 and 206. Such a configuration is generally referred to as a four-point measurement. The four-point measurement scheme employs a very low magnitude sense current 218 relative to test current 226 so that a voltage drop resulting from sense current 218 can be considered negligible. As a result, the resistance measured by ohmmeter 210 can be assumed to represent the resistance of only sample 31.

FIG. 13 is a perspective view illustrating PTP transformer 100 of FIG. 12, according to one embodiment. As illustrated, stationary structure 102 includes external contacts 230, 232, 234, and 236, and ground contacts 240, 242, and 244. External contacts 230 and 234 are respectively connected to sample contacts 200 and 204 of moveable structure 104 via conductive traces 250 and 254 which are respectively routed across a top surface of springs 107 and 108. External contacts 232 and 236 are respectively connected to sample contacts 202 and 206 via conductive traces 252 and 256. With reference to FIG. 12, external leads of voltmeter 216 and power supply 224 are respectively coupled to external contacts 230, 234 and external contacts 232, 236 of stationary structure 102 of PTP transformer 100. External contacts 230, 232, 234, 236 and leads 250, 252, 254, 256 are electrically isolated from device layer 140 by a silicon dioxide layer between device layer 140 and the metal electrodes.

Ground contacts 240 and 244 are connected to stationary structure 102 and to moveable structure 104 via springs 105 and 106, respectively, and ground contact 244 is connected to stationary structure 102. It is noted that a large portion of a surface of device layer 140 of PTP transformer 100 (see FIG. 6) comprises a ground electrode, which helps to eliminate electron charge on PTP transformer 100 and thereby reduces error which might otherwise be caused by an undesirable electrostatic interaction between PTP transformer 100 and a tip of displaceable electrode 34 of EM transducer 32 (see FIG. 1). Such a ground connection and resulting electrical discharge is especially important for in-situ electron microscopy tests (e.g. transmission electron microscopy (TEM) and/or scanning electron microscopy (SEM)) which require removing the tip-device attraction resulting from the electrical potential between the two.

FIG. 14 is a microscope image 250 of fabricated PTP transformer 100 as illustrated by FIGS. 12 and 13 above. In image 250, pulling gap 118 has a width of approximately 4 μm.

Figure 15:
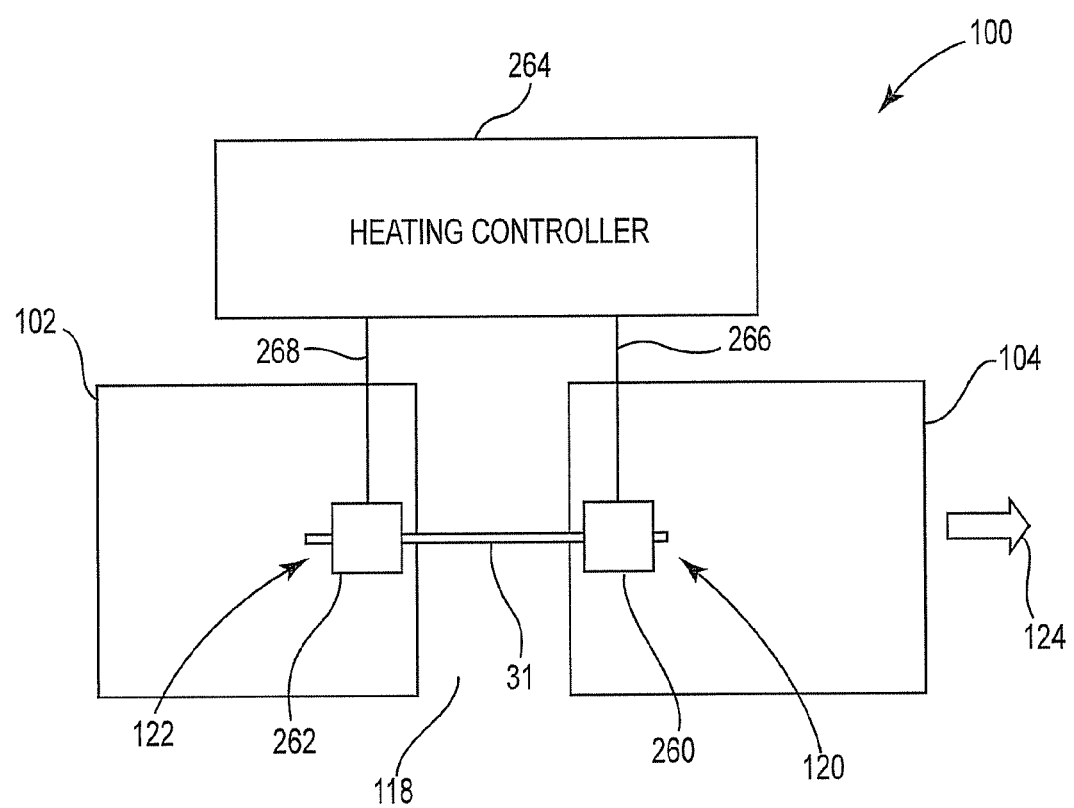
FIG. 15 is a schematic diagram of a thermal-mechanical tensile test according to one embodiment.

FIG. 15 is a block and schematic diagram generally illustrating PTP transformer 100, according to one embodiment. A first resistive heater 260 is formed in sample mounting area 120 of moveable structure 104, and a second resistive heater 262 is formed in sample mounting area 122 of stationary structure 102. Resistive heaters 260 and 262 are electrically connected to a heating controller 264 via leads 266 and 268, respectively, wherein leads 266 and 268 are similar to leads/contacts described above by with respect to FIG. 13 (e.g. external contacts 230, 232 and conductive traces 250, 252). Test sample 31 is coupled at each end proximate to resistive heaters 260, 262 and spans pulling gap 118. During a tensile testing process, test sample 31 is heated by heating controller 264 via heaters 260, 262. Upon reaching a desired or set temperature, test sample is mechanically characterized by applying a pushing force to moveable structure 104 via an actuator, such as displaceable electrode 34 of EM transducer 32 (see FIG. 1). Although not illustrated, it is noted that a temperature sensor can be integrated with resistive heaters 260, 262 so that a temperature of test sample 31 can be monitored by heating controller 264 during a tensile testing procedure.

With reference to FIGS. 11, 12, and 15 above, it is noted that both ohmmeter 210 and heating controller 264 may comprise stand-alone devices separately coupled to PTP transformer 100, or may be incorporated as part of controller 50 of nanomechanical test system 30 (see FIG. 1).

In summary, the present disclosure provides PTP linear mechanical transformer 100 for tensile testing of micrometer to nanometer scale structures. PTP linear mechanical transformer 100 converts a pushing force into pulling force by employing sample mounting areas 120 and 122 which are positioned on opposite sides of pulling gap 118 formed by stationary structure 102 and movable structure 104. To provide measurement accuracy and stability during tensile testing of a test sample 31, movable structure 104 aligns a pushing force and the resulting pulling force along a same force axis, such as along centerline 112 of PTP transformer 100. In addition to aligning the pushing and pulling forces, moveable structure 104 is coupled to stationary structure 102 via at least one spring, such as springs 105-108, which are configured to provide moveable structure 104 with a higher stiffness to the lateral and vertical directions 152, 154 as compared to tensile extension direction 124. The alignment of the pushing and pulling forces, and the stiffness characteristics of moveable structure 104 reduce undesirable effects that lateral and vertical direction forces may otherwise have on the tensile testing process. PTP transformer 100 can be used for in-situ electron microscopy tensile testing and, by adding conductor traces and heating elements, can also be employed for performing electromechanical and thermal-mechanical tensile testing.

Tensile test holder 52 employing PTP transformer 100, according to the present disclosure, also provides additional benefits as compared to conventional test holders. First, MEMS based PTP transformer 100 can serve as an accurate force calibrator for any device which requires a stiffness calibration or force calibration, such as electromechanical transducers, for example. In one instance, a device to be calibrated can be pushed against moveable structure 104 of PTP transformer 100, and based on the resulting displacement and known stiffness of moveable structure 104, the force exerted by the device to be calibrated can be estimated. Compared to an atomic force microscope (AFM) cantilever, which has been widely used for force calibration, PTP transformer 100 offers the following advantages: (1) a large linear relationship between displacement and force; (2) high structural stability (e.g. stiffness) and one-dimensional movement; (3) a relatively large physical dimension which enables in-situ force calibration, even under optical microscopes; (4) a stiffness which can be designed to match specific stiffness requirements and (5) low-cost fabrication.

Second, MEMS based PTP transformer 100 can serve as a very high accuracy and resolution strain sensor which is particularly useful for measuring strain after failure of a test sample. As described above, because both ends of a test sample are fixed along a force axis (e.g. centerline 112), the fractured surfaces of a test sample will match to one another after retracting the external testing or pushing force.

Third, MEMS based PTP transformer 100 can be employed to measure a relationship between an attraction force and distance between the fractured surfaces of a failed test sample. Because of the single axis movement of moveable structure 104, the fractures surfaces will match to one another after retracting of the external pushing force. A resolution is determined by EM transducer 32.

Fourth, MEMS based PTP transformer 100 can effectively protect a test sample from potential pre-test failure resulting from a power-on of the actuation device (e.g. EM transducer 32). Generally, when an electronic device is powered on, the actuation device is accompanied by some vibration. For bulk mechanical testing, the vibration is comparatively small and is not of concern. However, for nanomechanical testing, such vibration may be sufficient to cause failure of the test sample.

Also, MEMS based PTP transformer 100 simplifies sample preparation from a 3-dimensional process to a one-dimensional process because both sides of pulling gap 118 are on a same plane so that the test sample needs only to be aligned along an axis perpendicular to pulling gap 118. Additionally, the springs of MEMS based PTP transformer 100, such as springs 105-108, act as energy buffers upon failure or yield of test sample 31 and ensure the stability of the test system. Furthermore, since MEMS based PTP transformer 100 has a much higher natural frequency (e.g. greater than ten times) than the actuation and sensing devices (e.g. EM transducer 32), the resolution of the actuation and sensing devices is not sacrificed.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A microelectromechanical device for testing micro-to-nanoscale material samples comprising:
   a first structure; and
   a second structure disposed relative to the first structure to form a pulling gap there between, the second structure coupled to the first structure by at least one resilient element such that when a pushing force is applied to and pushes the second structure in a tensile extension direction the at least one resilient element compresses and a width of the pulling gap decreases to apply a tensile force to a test sample mounted across the pulling gap.

2. The microelectromechanical device of claim 1, wherein the pulling gap intersects a pushing force axis along which the pushing force is applied.

3. The microelectromechanical device of claim 2, wherein the force axis comprises a centerline of microelectromechanical device.

4. The microelectromechanical device of claim 1, including a pair of pushing gaps between the first and second structures, the pulling gap positioned between the pair of pushing gaps, wherein a width of each of the pushing gaps of the pair of pushing gaps decreases when the pushing force is applied to and pushes the second structure in the tensile extension direction.

5. The microelectromechanical device of claim 1, wherein the pair of pushing gaps and the pulling gap intersect a pushing force axis along which the pushing force is applied.

6. The microelectromechanical device of claim 1, wherein the test sample is mounted across the pulling gap between a first sample mounting area on the first structure and a a second sample mounting area on the second structure.

7. The microelectromechanical device of claim 6, wherein the first and second sample mounting areas are disposed on a pushing force axis along which the pushing force is applied.

8. The microelectromechanical device of claim 6, wherein a first resistive heater is disposed at the first sample mounting area and a second resistive heater is disposed at the second sample mounted area, the first and second resistive heaters configured to heat the test sample to a desired temperature.

9. The microelectromechanical device of claim 1, wherein the at least one resilient element is configured with a stiffness to allow movement of the second structure in the tensile extension direction and to resist movement of the second structure in directions other than the tensile extension direction.

10. A method of testing micro-to-nanoscale material samples comprising:
    mounting a micro-to-nanoscale material sample across a pulling gap between a first structure and a second structure of a microelectromechanical test structure, the first and second structures coupled to one another with at least one resilient element; and
    pushing the second structure with a pushing force that compresses the at least one resilient element and increases a width of the pulling gap so as to apply a tensile force to the material sample.

11. The method of claim 10, including measuring an electrical resistance of the material sample as the pushing force pushes the second structure.

12. The method of claim 10, wherein measuring the electrical resistance comprising using one of a two-point measurement scheme and a four-point measurement scheme.

13. The method of claim 10, including passing a test current through the material sample as the pushing force pushes the second structure.

14. The method of claim 10, including heating the material sample to a desired temperature after it has been mounted across the pulling gap and prior to pushing the second structure.

15. The method of claim 10, wherein pushing the second structure with a pushing force comprises pushing the second structure with a nanonindenter.

16. The method of claim 15, including measuring the pushing force and the increase in width of the pulling gap with the nanoindenter and determining a force-displacement curve for the material sample based on the measurements.

17. The method of claim 10, including keeping the first structure stationary relative to the second structure while pushing the second structure.

18. The method of claim 10, including recording a stream of transmission electron microscopy images of the material sample as the pushing force pushes the second structure.

19. A method of tensile testing micro-to-nanoscale material samples comprising
    applying a pushing force along an actuation axis to a push-to-pull mechanical transformer having a pulling gap across which a micro-to-nanonscale sample is mounted, the micro-to-nanoscale sample being positioned on the actuation axis;
    converting the pushing force, with the push-to-pull mechanical transformer, to a tensile force which is applied to the micro-to-nanonscale sample via an increase in a width of the pulling gap in response to the pushing force.

20. The method of claim 19, wherein applying a pushing force includes applying the pushing force with a nanoindenter, and further including measuring the pushing force and the increase in width of the pulling gap with the nanoindenter and determining a force-displacement curve for the material sample based on the measurements.

* * * * *